United States Patent [19]
Griffiths et al.

[11] Patent Number: 5,728,369
[45] Date of Patent: Mar. 17, 1998

[54] RADIOACTIVE PHOSPHORUS LABELING OF PROTEINS FOR TARGETED RADIOTHERAPY

[75] Inventors: Gary L. Griffiths, Morristown; Hans J. Hansen, Mystic Island; Habibe Karacay, Matawan, all of N.J.

[73] Assignee: Immunomedics, Inc., Morris Plains, N.J.

[21] Appl. No.: 318,917

[22] Filed: Oct. 5, 1994

[51] Int. Cl.$^6$ .................... C07K 1/13; A61K 39/44; A61K 51/10

[52] U.S. Cl. .................... 424/149; 424/153; 424/173; 424/177; 424/179.1; 530/391.3; 530/391.5; 530/404; 530/405; 530/408; 530/409

[58] Field of Search .................... 530/345, 391.3, 530/391.5, 404, 405, 408, 409; 424/1.49, 1.53, 1.73, 1.77, 179.1

[56] References Cited

FOREIGN PATENT DOCUMENTS 2262528  12/1992  United Kingdom.
WO 90/11289  of 0000  WIPO.

OTHER PUBLICATIONS

Cook, "Medicinal Chemistry of Antisense Oligonucleotides Future Opportunities", *Anti–Cancer Drug Design*, 6: 585–607 (1991).
Goodchild (1990) Biocoyulate Chem. 1(3):165–187.
Schmidt et al. FEBS Lett. 194:305 (1986).
Hwang et al. *Biochim. Biophys. Acta* 882:331 (1986).
De Boer et al. *Clin. Exp. Immunol.* 3:865 (1968).
Clertant et al. *J. Biol. Chem.* 257:6300 (1982).
Foxwell et al. *Brit. J. Cancer* 57:489 (1988).
Craeighton et al. "The development of $^{32}$P technology for radioimmunotherapy" in Monoclonal Antibodies 2. Applications in Clinical Oncology, A.A. Epenetos, ed., Chapman and Hall, (1993) pp. 103–109.

*Primary Examiner*—Ponnathapura Achutamurthy
*Attorney, Agent, or Firm*—Foley & Lardner

[57] ABSTRACT

$^{32}$P- and $^{33}$P-labeled proteins which are useful for radiotherapy are prepared by stably linking $^{32}$P- or $^{33}$P- containing molecules to targeting proteins in such a way that the targeting protein retains the ability to bind to a cellular target. Methods for preparing the labeled proteins and their use in methods of radiotherapy are described.

13 Claims, No Drawings

RADIOACTIVE PHOSPHORUS LABELING OF PROTEINS FOR TARGETED RADIOTHERAPY

BACKGROUND OF THE INVENTION

The present invention relates to phosphorus-32 and phosphorus-33 labeled proteins which are useful for radiotherapy. In particular the invention relates to methods of stably linking $^{32}$P- and $^{33}$P-containing molecules to targeting proteins in such a way that the targeting protein retains the ability to bind to a cellular target. This invention also relates to methods of therapy using the labeled proteins.

Many radionuclides have been studied for their suitability for internal administration to patients in radiotherapy. Some radionuclide compounds, containing isotopes such as $^{131}$I, can be given systemically, taking advantage of the fact that these elements tend to localize to particular tissues by virtue of their chemical properties. Other radionuclides, such as $^{198}$Au and $^{103}$Pd have been administered in a localized fashion, for instance to the site of a tumor. Most recent approaches, however, have focused on methods of delivering radionuclides to a preselected tissue by attaching the radionuclide to a targeting protein, usually an antibody, which will then localize to that tissue.

A large number of methods for linking radionuclides to antibodies have been developed. The chemical toxicity of many radionuclides means that complex methods must often be used to stably bind the isotope to an antibody. For example, to use $^{90}$Y, which has many desirable radiochemical properties, a chelate must be synthesized and covalently bound to the antibody to stably link the radioisotope to the antibody.

One isotope which displays many of the same desirable features as $^{90}$Y, but which has received little attention for targeted radiotherapy, is $^{32}$P. $^{32}$P is inexpensive, is readily available in high specific activity in a variety of labeled molecules, and has a therapeutically desirable half-life of 14 days. It is absorbed by the body and is not readily excreted, and is therefore amenable to use in outpatient procedures. In addition, $^{32}$P emits only β-radiation with an excellent depth penetration in tissue of approximately 6 mm. Unlike many other radionuclides under consideration for targeted radiotherapy, it is not inherently toxic, and is currently used clinically in some non-targeted applications, for example for the treatment of ovarian cancer and polycythemia rubra vera.

Another radioisotope of phosphorus, $^{33}$P, has received even less attention than $^{32}$P. $^{33}$P shares the same chemical properties as $^{32}$P, and has similarly desirable radiochemical characteristics. It is available in high specific activity, and has a 25-day half life with a β-particle emission energy of 0.25 MeV, approximately 15% of the value of the β-emission energy of $^{32}$P.

The reason radioactive phosphorus has received relatively little attention for targeted radiotherapy applications has been the difficulty of linking it to targeting proteins. Most of the methods currently known are non-specific and slow, and do not efficiently incorporate radionuclide into the targeting protein.

One very general method of labeling proteins with $^{32}$P is simply to incubate the protein with α-$^{32}$P-labeled nucleoside triphosphates. Schmidt et al., *FEBS Lett.* 194:305 (1986). The mechanism for the labeling reaction is unknown. The method is slow and gives only poor incorporation of label (less than 1% of the protein molecules are labeled), and is thus too inefficient for therapeutic use.

A second general method of $^{32}$P labeling is to incubate proteins with [γ-$^{32}$P]ATP or H$_3$$^{32}$PO$_4$ in the presence of chromium ions. Hwang et al., *Biochim. Biophys. Acta* 882:331 (1986). This method is relatively rapid, but gives an unknown level of label incorporation and also leaves toxic chromium ions bound to the proteins, which would be therapeutically unacceptable.

A third general method is the use of $^{32}$P-diphenylphosphinothioic chloride as a reactive labeling compound. De Boer et al., *Clin. Exp. Immunol.* 3:865 (1968). This reagent is thought to react non-specifically with lysine residues in proteins to form a highly stable conjugate, but approximately 50% of the radioactivity also associates non-covalently with the labeled protein. Although this method allows labeling of proteins to high specific activity, the labeling agent is only poorly water soluble, and to achieve good labeling yields large excesses of reagent must be used, wasting relatively large amounts of hazardous radioactive materials.

A less general method of $^{32}$P labeling is the use of periodate-oxidized [α-$^{32}$P]ATP to affinity-label proteins containing an ATP-binding site. Clertant et al., *J. Biol. Chem.* 257:6300 (1982). Because many targeting proteins which are of therapeutic interest, in particular antibodies, do not contain ATP-binding sites this method is therefore of little general utility.

A more recent method, intended for labeling antibodies for radiotherapy, involves the chemical conjugation of protein kinase substrate peptides to antibodies. Foxwell et al., *Brit. J. Cancer* 57:489 (1988). The conjugates are labeled by treatment with [γ-$^{32}$P]ATP in the presence of the catalytic subunit of cAMP-dependent protein kinase (protein kinase A, PKA), which transfers $^{32}$P-phosphate to a serine residue in the substrate peptide. This method showed differences in the β-phase half-life between the $^{32}$P-labeled antibody and a corresponding $^{131}$-I-labeled antibody, and also high $^{32}$P uptake in the bone of animals injected with the labeled antibody. Creighton et al., "The development of $^{32}$P technology for radioimmunotherapy" in MONOCLONAL ANTIBODIES 2. APPLICATIONS IN CLINICAL ONCOLOGY. A. A. Epenetos, ed., Chapman and Hall, (1993) pp. 103–109. These results indicate in vivo instability of the label, presumably due to the action of protein phosphatases which are ubiquitous in eukaryotic cells.

It is apparent therefore, that new methods for $^{32}$P- and $^{33}$P-labeling targeting proteins are greatly to be desired. In particular, new methods in which the $^{32}$P or $^{33}$P label is stable in vivo and which do not compromise the binding abilities of these proteins are needed.

SUMMARY OF THE INVENTION

It is therefore an object of this invention to provide methods for stably labeling targeting proteins with $^{32}$P or $^{33}$P.

It is a further object of this invention to provide targeting proteins which are stably labeled with $^{32}$P or $^{33}$P and which are useful for radiotherapy.

It is yet a further object of this invention to provide pharmaceutical compositions containing $^{32}$P- or $^{33}$P-labeled proteins for radiotherapy of patients suffering from a tumor or infectious lesion.

It is a still further object of this invention to provide kits for stably labeling targeting proteins with $^{32}$P or $^{33}$P.

It is a still further object of this invention to provide a method of radiotherapy of a patient suffering from a tumor or an infectious lesion, wherein a targeting protein that specifically binds to a complementary molecule or structure produced by, or associated with, a tumor or an infectious lesion, and radiolabeled with $^{32}$P or $^{33}$P, is parenterally injected into a human patient suffering from said tumor or infectious lesion.

In accordance with these objectives there has been provided a radiolabeled targeting protein comprising a complex of the formula Q—(S)$_m$—L—NR'—P(O)(OH)Y—R, in which P is the $^{32}$P or $^{33}$P isotope, Q is a protein capable of binding specifically to a complementary target molecular species by virtue of a complementarity-determining region thereof, L is a linker moiety, Y is oxygen or a single bond to R, or Y is NR", R, R', and R" are the same or different, and each is an optionally substituted straight-chain or branched-chain alkyl, cycloalkyl, aryl, or heterocyclic group containing from 1 to 20 carbon atoms, or is hydrogen, and wherein m is 1 or 2, or a physiologically acceptable salt thereof.

In a preferred embodiment Q is a monoclonal antibody or antibody fragment, and in another preferred embodiment the thiol group on Q is generated by reduction of a disulfide bond in the hinge region of this monoclonal antibody or antibody fragment.

In a further preferred embodiment, L is —S—A—, in which A is an optionally substituted saturated or unsaturated straight-chain or branched-chain alkylene, cycloalkylene, arylene, or divalent heterocyclic group containing from 1 to 20 carbon atoms. In yet another preferred embodiment L is —CH$_2$—CO—BD—, in which B is O, NH, or B is a single bond to C, and D is an optionally substituted saturated or unsaturated straight-chain or branched-chain alkylene, cycloalkylene, arylene, or divalent heterocyclic group containing from 1 to 20 carbon atoms.

In still another preferred embodiment L is

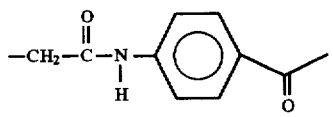

In still another preferred embodiment L is

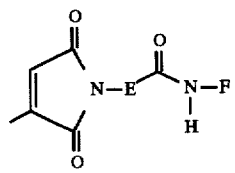

wherein E and F are the same or different, and each is an optionally substituted saturated or unsaturated straight-chain or branched-chain alkylene, cycloalkylene, arylene, or divalent heterocyclic group containing from 1 to 20 carbon atoms. A still further preferred embodiment is when E is selected from the group consisting of:

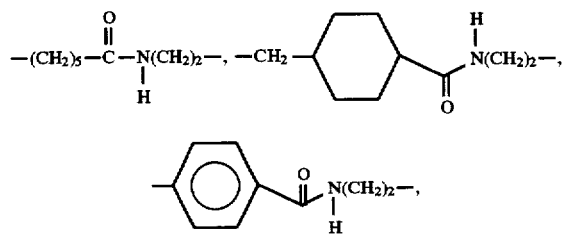

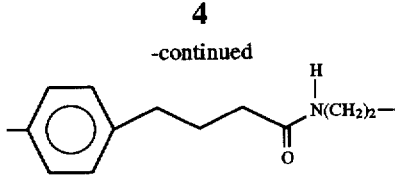

and F is (CH$_2$)$_2$.

In yet another preferred embodiment YR is selected from the group consisting of 5'—O-adenosine, 5'—O-guanosine, 5'—O-thymidine, 5'—O-cytidine, 5'—O-deoxyadenosine, 5'—O-deoxyguanosine, 5'—O-uridine, 5'—O-deoxycytidine, 5—O-inositol-1,4-bisphosphate and 5—O-inositol-1,3,4-trisphosphate.

In accordance with another embodiment of the invention there has been provided a pharmaceutical composition, comprising an effective amount of a radiolabeled targeting protein as described above, in a pharmaceutically acceptable sterile vehicle.

In accordance with yet another embodiment of the invention there has been provided a method of preparing a radiolabeled targeting protein, by contacting a protein capable of binding specifically to a complementary target molecular species by virtue of a complementarity-determining region thereof, and containing at least one free thiol group, with a complex of the formula L'—NR'—P(O)(OH)Y—R, in which in which P is the $^{32}$P or $^{33}$P isotope, L' is a linker moiety containing a group capable of reacting specifically with thiol groups on the targeting protein to form a disulfide or thioether linkage, Y is oxygen or a single bond to R, or Y is NR", and R, R', and R" are the same or different, and each is an optionally substituted straight-chain or branched-chain alkyl, cycloalkyl, aryl, or heterocyclic group containing from 1 to 20 carbon atoms, or is hydrogen, or a physiologically acceptable salt thereof.

In accordance with still another embodiment of the invention there has been provided a method for treating a disease in a mammal, comprising administering to a mammal in need thereof a radiolabeled targeting protein comprising a radiolabeled targeting protein as described above.

In accordance with another embodiment of the invention there has been provided a kit for preparing a radiolabeled targeting protein comprising, in suitable containers, (1) a preparation of a bifunctional cross-linking molecule comprising: a moiety comprising a group capable of reacting specifically with thiol groups on a protein to form a disulfide or thioether linkage, and a primary or secondary amine group; (2) a targeting protein containing at least one thiol group; and (3) at least one reagent for effecting coupling between a phosphate, phosphonate, or phosphoramidate P—OH and the primary amine group.

DETAILED DESCRIPTION

The present invention provides a simple method of labeling targeting proteins with $^{32}$P or $^{33}$P. A $^{32}$P- or $^{33}$P-labeled phosphate compound is coupled to a linker molecule which is conjugated to reactive groups on the targeting protein. The protein-phosphorus linkage is stable in vivo against both chemical and enzymatic degradation. The labeled targeting proteins bind specifically to diseased cells or tissue, which are killed by the radiation from the $^{32}$P or $^{33}$P. The invention also includes pharmaceutical compositions comprising an effective amount of at least one of the $^{32}$P- or $^{33}$P-labeled targeting proteins of the invention in combination with a pharmaceutically acceptable sterile vehicle, as described, for example, in Remingtons' Pharmaceutical Sciences; Drug Receptors and Receptor Theory, 18th ed., Mack Publishing Co., Easton, Pa. (1990). The invention also includes kits for labeling targeting proteins which are convenient and easy to use in a clinical environment.

The targeting proteins used in the invention preferentially bind to cells and tissues which are associated with a disease state and, by killing these cells or tissues, alleviate the disease state. This binding occurs to complementary molecules and structures associated with or expressed on the surface of the diseased cells or tissue, which preferably are not associated with or expressed on the surface of healthy cells. More typically the complementary moieties will be present on healthy cells, but to a lesser extent than is observed in the disease state. For example, many tumors show large increases in expression of the epidermal growth factor (EGF) receptor compared to normal tissue. $^{32}$P- or $^{33}$P-labeled proteins targeted at the EGF receptor will bind preferentially to such tumor cells, leading to a high effective concentration of $^{32}$P or $^{33}$P and causing preferential cell killing at the site of the tumor. Another example is carcinoembryonic antigen (CEA) which is highly expressed on the surface of many tumors. A $^{32}$P- or $^{33}$P labeled antibody or antibody fragment which binds to CEA will cause preferential cell killing at the tumor site.

For the purposes of chemical and enzymatic reactivity, $^{32}$P and $^{33}$P labeled molecules behave identically. It will be understood therefore that reference hereafter to labeling with $^{32}$P will also encompass labeling with $^{33}$P.

A. Methods for Preparing $^{32}$P-Labeled Compounds Suitable for Coupling to Targeting Proteins The $^{32}$P-labeled compounds which are to be coupled to the targeting proteins are prepared by linking, via a phosphoramidate linkage, a moiety which reacts specifically with reactive groups on a protein to a $^{2}$P-phosphate ester. This requires the preparation of a bifunctional linker which contains both a nucleophilic amine group, to allow formation of the phosphoramidate linkage, and a group capable of coupling to the protein.

The bifunctional linker can be coupled to the protein by means which are known in the art. For example, a linker containing an active ester moiety, such as an N-hydroxysuccinimide ester, can be used for coupling to lysine residues in the protein via an amide linkage. In another example, a linker containing a nucleophilic amine or hydrazine residue can be coupled to aldehyde groups produced by glycolytic oxidation of protein carbohydrate residues. See U.S. patent application Ser. No. 08/162,912, which is hereby incorporated by reference in its entirety. In addition to these direct methods of coupling, the linker can be indirectly coupled to the protein by means of an intermediate carrier such as an aminodextran. See, for example, U.S. Pat. No. 5,057,313, which is hereby incorporated by reference in its entirety. In these embodiments the modified formula Q—NH—L—NR'—P(O)(OH)Y—R represents the linkage via either lysine, carbohydrate, or an intermediate carrier.

In a preferred embodiment, the linker is coupled site-selectively to free thiol residues in the protein. Moieties which are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine. Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavoured. An example of an α-halo carboxyl linker suitable for practice of the invention is succinimidyl-4-(iodoacetylamido)benzoate (1).

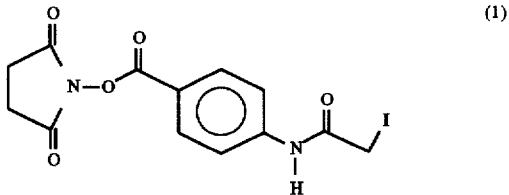

In a preferred embodiment of the current invention the thiol-selective coupling moiety is a maleimide. Maleimide-containing linkers are well known in the art. See, for example, Wong, "CHEMISTRY OF PROTEIN CONJUGATION AND CROSSLINKING" (CRC Press, Boca Raton, 1991) pp 152–164. Several suitable maleimide compounds are commercially available from Pierce Chemical Co. (Rockford, Ill.). Examples of these compounds are SMCC (2), SMPB (3), MBS (4), and EMCS (5).

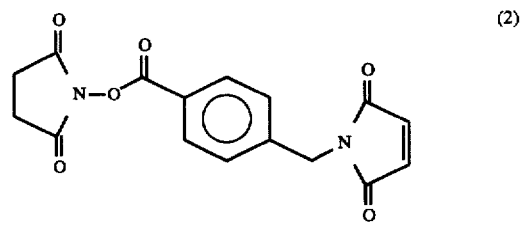

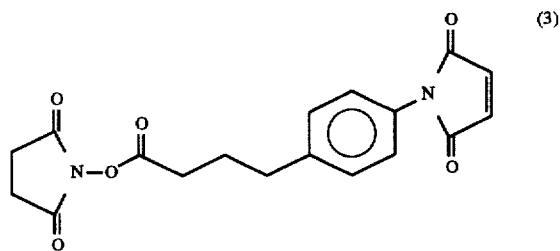

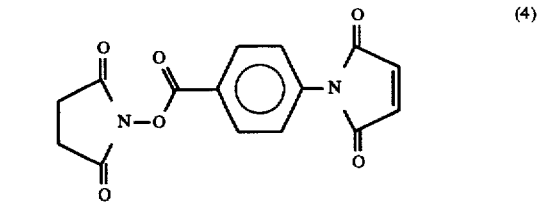

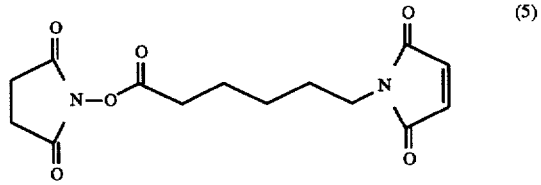

The maleimide-containing linkers known to the art do not contain the nucleophilic amine group required by the current invention. Thus, if known linkers are to be used the amine function must be introduced. Most of the linkers known to the art, including compounds (1) through (5), contain a group, typically an N-hydroxysuccinimide ester, which will preferentially react with an amine to form an amide function.

Reaction of the linker with a diamine compound therefore serves to introduce the desired amino function. For example, reaction of SMCC with ethylenediamine will give compound (6), which contains a thiol-specific maleimide group and a nucleophilic amine group. Use of an excess of diamine serves to prevent the formation of cross-linked maleimides formed by the reaction of two molecules of SMCC with a single diamine group. Diamines suitable for use in the present invention are well known to one of ordinary skill in the art, and include compounds in which the two amino groups are linked by a straight or branched-chain alkyl or cycloalkyl group containing up to 20 carbons, or by a substituted or unsubstituted aryl group.

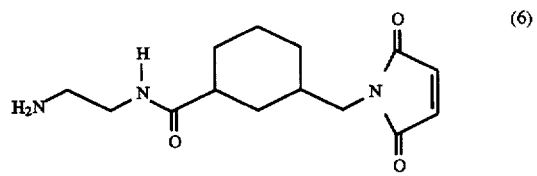

(6)

In an alternative preferred embodiment the desired bifunctional linker can be synthesized by reaction of a monoprotected diamine with maleic anhydride to form a maleimide, followed by deprotection of the amine. This reaction is illustrated in Reaction Scheme I below. The amine protecting group is preferably a 'butoxycarbonyl (Boc) group which is removed by treatment with trifluoroacetic acid. The mono-Boc-protected diamine is preferably prepared by reacting an excess of a diamine with di'butyl-dicarbonate. The diamines suitable for coupling to known linkers as described above are also suitable for use in Reaction Scheme I.

Reaction Scheme I

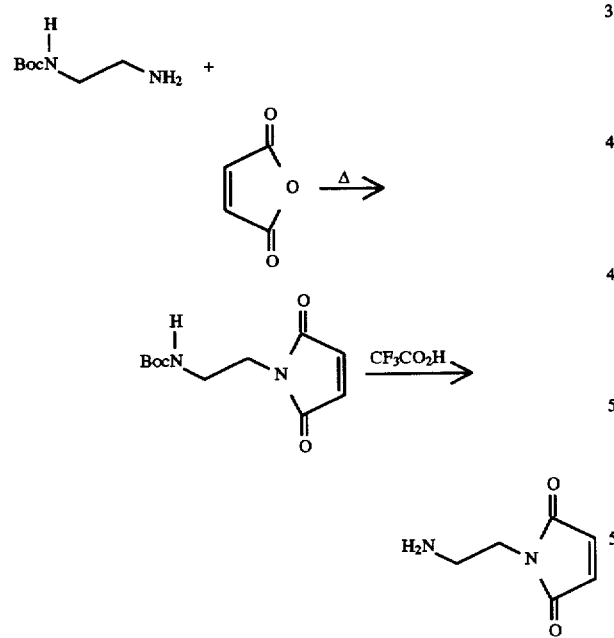

Once the bifunctional linker is prepared it must be coupled to a reactive $^{32}$P-compound to form a linking compound containing a phosphoramidate bond. The invention can be practiced with any $P^{III}$ or $P^V$ phosphorus compound capable of forming a phosphoramidate bond which is stable under in vivo conditions, and is limited only by the commercial availability of $^{32}$P or $^{33}$P-radiolabeled materials. Commercially available radiophosphorus compounds are presently limited to $^{32}$P-labeled nucleoside mono-, di-, and triphosphates, inositol phosphates, phosphoric acid and sodium phosphate, and $^{33}$P-labeled nucleoside triphosphates and phosphoric acid, but it is the inventors' intention that the current invention encompass the use of any suitable new $^{32}$P- or $^{33}$P-labeled compounds which become available.

Suitable methods that use $P^{III}$ compounds to form the phosphoramidate bond are well known in the art. For example, the phosphoramidate bond to the bifunctional linker is formed by oxidatively coupling the linker amine to a phosphite triester in the presence of iodine (Jager et al., Biochem. 27:7237 (1988)) or carbon tetrachloride/pyridine (Froehler et al., Nucl. Acids. Res. 14:3487 (1986); id. 16:4831 (1988)). Use of β-cyanoethyl phosphite esters allows subsequent selective deprotection of the esters under mildly basic conditions which do not affect the maleimide moiety.

Methods of coupling amines to phosphates to form phosphoramidates are well known to the skilled practitioner. All of the known methods involve the temporary activation of the phosphate group via conversion of one the phosphate oxygen groups into a leaving group which is displaced by the amine. The coupling can be carried out using triphenylphosphine and dipyridyldisulfide as the coupling agents, during which a phosphate oxygen is activated by forming a bond to the phosphorus atom of the triphenylphosphine. See, for example, Greene et al., Nucl. Acids Res. 2:1123 (1975). In a preferred embodiment the coupling is carried out using a carbodiimide as a coupling agent. See Moffat et al, J. Amer. Chem. Soc. 83:649 (1961); Bergstrom et al., Biochim. et Biophys. Acta 1061:95 (1991); Ohtsuka et al., Nucl. Acids Res. 3:653 (1976). The carbodiimide is preferably a water-soluble carbodiimide such as 1-ethyl-3-(3-dimethylaminopropyl)carbodiimide hydrochloride (EDC), which is available from Pierce Chemical Co. (Rockford, Ill.). The reaction is carried out by mixing the $^{32}$P-labeled phosphate with the bifunctional linker and carbodiimide in a stoichiometric ratio in an aqueous solvent. After one to two hours (the time of reaction is not critical) the mixture is used directly for coupling to the targeting protein. The choice of solvent is not critical, but the reactants must be soluble in it, it must not interfere with the reaction, and it must be miscible with water for the protein-linking step. Preferred solvents include DMF, DMSO, and 'butyl alcohol. The reaction of adenosine monophosphate with linking compound (6) is shown in Reaction Scheme II and is illustrative of the coupling reaction. The by-products of the reaction need not be removed at this stage as they will be removed during the rapid purification step after linking of the radiolabeled compound to the targeting protein.

Reaction Scheme II

Scheme II

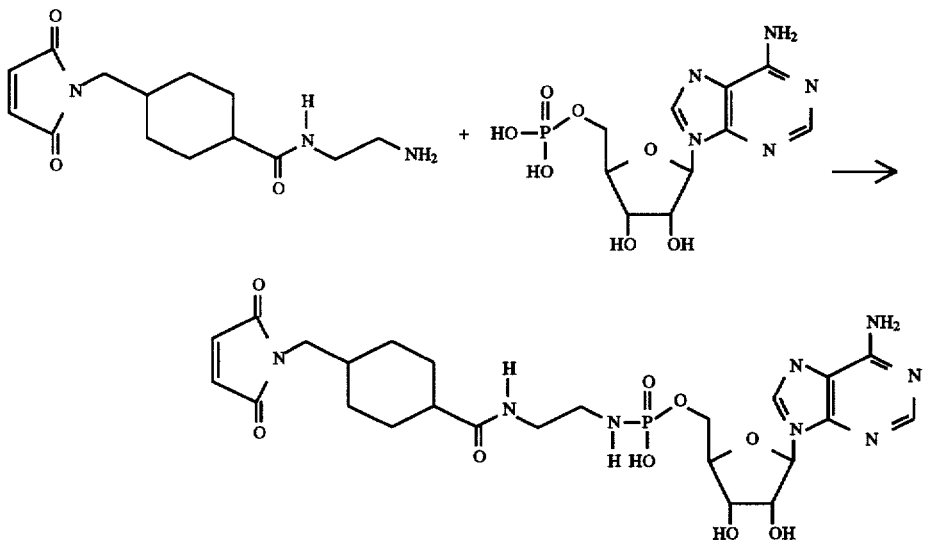

In a preferred embodiment the phosphate is selected from $^{32}$P-labeled adenosine 5'-monophosphate, thymidine 5'-monophosphate, guanosine 5'-monophosphate, cytosine 5'-monophosphate, uridine 5'-monophosphate, and inositol 1-monophosphate, all of which are commercially available from DuPont-NEN (Boston, Mass.), Amersham International (Arlington Heights, Ill.) or ICN (Costa Mesa, Calif.).

The invention can also be practiced with phosphonates capable of forming stable amidophosphonate compounds. The methods described above for coupling amines to phosphate compounds can also be used to prepared amidophosphonates.

B. Coupling of $^{32}$P-labeled Compounds to the Targeting Protein

The targeting proteins of the invention encompass any protein which binds with specificity to molecules or tissue structures that are implicated in disease. Examples of such targeting proteins include, but are not limited to: antibodies and antigen-binding fragments of antibodies; lymphokines, cytokines, and peptide growth factors; and lymphokine or cytokine receptor antagonists. In a preferred embodiment the targeting protein is a monoclonal antibody or an antigen binding fragment of a monoclonal antibody.

In a preferred embodiment the targeting protein contains thiol groups which can react with the $^{32}$P-labeled compounds prepared as described above. The thiol group may be present as a cysteine residue, or may be introduced, either via reduction of disulfide (cystine) residues or via thiolation of the protein. Thiolation of proteins is readily achieved by methods well known in the art. For example, lysine residues can react with Traut's reagent (2-iminothiolane) to form free thiol residues on the protein. Alternatively the protein can be thiolated by the methods described in U.S. patent application Ser. No. 08/253,772, which is herein incorporated by reference in its entirety.

In many cases the amino acid sequence of the protein will be available, and thus a ready determination can be made of whether a cysteine or lysine residue or a disulfide bond can be used to derivatize the protein by conjugation to the labeling agent. In some cases, however, thiolation, disulfide reduction, and direct coupling reactions must all be tested empirically to determine the optimum approach. The extent of conjugation can readily be determined by measuring the radioactivity bound per weight of protein after separation of protein from labeling agent via size exclusion chromatography.

The most common instance when the amino acid sequence of the targeting protein will be unknown will be when the targeting protein is a monoclonal antibody or antibody fragment. In such cases however, the structural features of antibodies confer a particular advantage for the practice of the invention. Antibody molecules are composed of two identical copies of heavy chains and light chains, covalently interconnected by disulfide bonds. For a general discussion, see Schultz et al., "Proteins II: Structure-Function Relationship of Protein Families," in TEXTBOOK OF BIOCHEMISTRY WITH CLINICAL CORRELATIONS, 3rd Ed., T. M. Devlin (ed.), Wiley & Sons, pp. 92–134 (1992); Turner et al., "Antigen Receptor Molecules," in IMMUNOLOGY, 3rd Ed., Roitt et al. (eds.), Mosby, pp. 4.1–4.20 (1993). The carboxyl-terminal one-half of light chains and the carboxyl-terminal three-quarters of heavy chains are highly conserved in amino acid sequence among antibodies with different antigen specificities, and are termed "constant regions". In contrast, the remaining regions of the light and heavy chains are highly variable among antibodies with different antigen specificities. Particular regions within these variable segments form the antigen binding site that is complementary to the topology of the antigen structure.

Proteolytic cleavage can be used to fragment an antibody into small, functional units. For example, proteolytic cleavage of an IgG molecule with papain cleaves the antibody in the hinge peptide of each heavy chain, producing a non-antigen binding "Fc" fragment made up of the C-terminal half of the heavy chains, and an identical pair of antigen binding "Fab" fragments, consisting of an amino-terminal segment of a heavy chain associated with an entire light chain. Fab fragments can bind antigen with an affinity similar to that of the intact antibody molecule.

Antibodies contain at least two disulfide bonds in the hinge region which link the two heavy chains, as well as disulfide bonds which join light and heavy chains together. The hinge region disulfide bonds are generally more accessible to disulfide reducing agents, and can normally be selectively cleaved. Provided that the reduction is performed under carefully controlled conditions the reduced fragments retain their immunospecificity and ability to bind to antigen. Furthermore, since sulfhydryl groups produced in the hinge region of an antibody or antibody fragment are sterically remote from the antigen binding site, coupling of chelating agents to these groups does not interfere with the binding activity of the antibody. Reduction of an antibody or F(ab')$_2$ fragment with known disulfide bond reducing agents, for example dithiothreitol, cysteine, mercaptoethanol and the like, gives after a short time, typically less than one hour, including purification, antibody having from 1–10 free sulfhydryl groups by analysis. It should be noted that if reducing conditions are too drastic, or the reducing agent is left in contact with the fragments for too long, the normally less reactive disulfide bonds linking light and heavy chains will eventually be reduced, with deleterious effects on the binding properties of the antibody. Carefully controlled reduction of antibodies results in preferential reduction of disulfide bonds on the hinge region of the antibody, and the resulting cysteine residues can then be used for the conjugation reaction of the invention.

When the targeting protein can be produced by recombinant DNA means, a suitable site for conjugation can be introduced by mutagenesis of the gene encoding the amino acid sequence of the protein. Methods for site-directed mutagenesis of genes are well known in the art. See, for example, Ausubel et al. (eds.), CURRENT PROTOCOLS IN MOLECULAR BIOLOGY, John Wiley & Sons (1987), ch.15.7, and Sambrook et al., MOLECULAR CLONING: A LABORATORY MANUAL, Second Edition, Cold Spring Harbor Laboratory, Cold Spring Harbor, N. Y. (1989). Typically the mutation will introduce at least one cysteine residue into the targeting protein at a site distal from the region required for the targeting activity of the protein. If multiple cysteine residues are engineered into the targeting protein by the methods described above, conjugation of the targeting protein with a plurality of $^{32}$P-labeled agents can be achieved, thus increasing the specific activity (radioactivity/mol protein) of the protein. Alternatively, the targeting protein produced by recombinant DNA means can have an IgG$_3$ or an IgG$_3$-like framework. Such a framework, having multiple hinge-region disulfide bonds, is particularly amenable to reductive processes in order to generate a multiplicity of free thiol groups. This will be advantageous for delivering the largest possible dose of radioactivity to a diseased cell or tissue.

The coupling reaction is carried out by mixing the labeling agent and the targeting protein in a suitable buffer and allowing reaction to proceed to completion. To achieve stoichiometric labeling of the protein the labeling agent can be used in a one to two-fold excess. Suitable buffers for carrying out the coupling reaction are well-known in the art. In a preferred embodiment the buffer is phosphate-buffered saline solution. The progress of the reaction is advantageously monitored using an HPLC size-exclusion column with an on-line radiation detector. Shift of radioactivity from the labeling agent to the protein indicates successful conjugation. The protein can also be tested for the presence of residual, unreacted, thiol groups by reaction with Ellman's reagent.

When the conjugation is complete the labeled protein is separated from excess labeling agent by size exclusion chromatography, for example on Sephadex G-50-80 resin in a spin column (Pharmacia, Piscataway, N.J.). The extent of labeling is measured by determining the specific radioactivity of the protein, that is the radioactivity per milligram of protein and comparing it to the value calculated based on the specific activity of the labeling agent, the molecular weight of the protein, and the number of thiol groups available for conjugation. The chemical purity of the labeled protein can be determined by using size-exclusion HPLC, for instance on a BioSil 250 column (Biorad, Hercules, Calif.) using UV detection. The UV detection trace can be compared to the trace produced by an on-line radioactivity detector during the same separation.

In all cases the conjugation of the protein must not deleteriously affect the targeting activity of the protein. In many cases mutated proteins with full targeting ability will have been prepared from the targeting protein, indicating those regions of the molecule which are essential for targeting ability. Whether a suitable conjugation site falls within such a region, or whether it is known that disulfide reduction renders a targeting protein inactive, is used to guide which particular approach to conjugation is to be used.

When the targeting protein is an antibody or antibody fragment which has been reduced by the procedure described above, the newly uncovered thiol groups are remote in space from the antigen binding site of the antibody, and therefore it may be predicted that conjugation to the labeling agents will not deleteriously affect the binding activity of the antibody.

In all cases it is preferred that the retention of binding activity of the targeting protein upon conjugation be confirmed empirically. This is done by measuring the binding activity of the protein before and after conjugation and comparing the results. For the purposes of the present invention, post-conjugation binding activity of 70% or more of the pre-conjugation activity indicates acceptable retention of binding. Methods for quantitatively measuring binding activity of targeting proteins are well known in the art. For example, if the targeting protein is a growth factor, standard cell culture assays of the growth factor activity can be used. If the targeting protein is a recombinant antibody, methods of measuring antibody affinity well known in the art, such as quantitative ELISA, can be used.

Simple kits for labeling targeting protein can be prepared to facilitate the practice of the invention in a clinical or research setting without the need for sophisticated laboratory equipment. The targeting protein is prepared in a suitable format for coupling as described above, such as by thiolation or disulfide reduction if necessary. The labeling protein is preferably provided in a frozen or lyophilized form in a vial, the contents of which are kept under vacuum or an inert atmosphere to ensure that free thiol groups are not oxidized. The vial is preferably capped with an air-tight septum seal or other means by which solutions can be added by injection in a sterile or semi-sterile fashion. In some instances a targeting protein which contains disulfide bonds may be provided in an unreduced form, together with reducing reagent and a simple protocol for carrying out reduction and purification as described above. In such cases purification materials, such as size-exclusion spin columns, such as Sephadex G-50-80 spin columns (Pharmacia) will be provided with the kit.

The kit will also contain the labeling agent in a form ready for $^{32}$P or $^{33}$P labeling. For example the agent in the vial will be lyophilized from a suitable buffer for reconstitution with $^{32}$P- or $^{33}$P-phosphate compound in aqueous solution. The vial will also preferably contain the cross-linking agent for coupling the phosphate to the labeling agent. The cross-linker is added to the labeling agent in the dry state and therefore no reaction will occur until the contents of the vial are reconstituted with the aqueous solution of the phosphate. The kit may also contain a vial of a $^{32}$P- or $^{33}$P-labeled phosphate suitable for carrying out the reaction. However, due to the short half-lives of $^{32}$P and $^{33}$P it is preferred that the radioactive material be obtained fresh from a commercial supplier shortly before it is used. Commercial suppliers of $^{32}$P and $^{33}$P compounds suitable for practicing the invention are well known in the art and include DuPont-NEN (Boston, Mass.), Amersham International (Arlington Heights, Ill.), and ICN Biomedicals (Costa Mesa, Calif.).

The labeled phosphate compound is added to the vial containing the labeling agent and the cross-linker, and after a prescribed time (determined previously using the methods described above), the contents of the vial are added to the vial containing the protein. After mixing, a specified amount of time is allowed to elapse and the labeled protein is purified on the provided size-exclusion column. In a preferred embodiment a spin column is used and is eluted with a physiologically compatible buffer, such as phosphate-buffered saline, so that the eluate may be used directly for administration to the patient.

C. Stability and Biodistribution of the Labeled Antibody

The stability of the radiolabeled protein conjugate under the physiological conditions in which it will be used can be determined by incubating the protein in human serum at 37° C. The incubation is preferably carried out in an atmosphere containing 5% $CO_2$ to maintain physiological pH. Samples are periodically removed and analyzed by polyacrylamide gel electrophoresis and size-exclusion chromatography, and the amounts of protein-bound and non-protein-bound radioactivity are quantitated.

The biodistribution of the labeled protein in vivo can be determined by experiments in rodents using techniques well known in the art. For example, the protein is injected into mice, and a predetermined number of mice are sacrificed for study after specified time periods. Bone is isolated by dissection and solubilized in an ethanol/nitric acid mixture. Tissue is solubilized using a tissue solubilized (such as the TS-1, available from Research Products International (Mount Prospect, Ill.). The radioactivity in the bone and tissue fractions are compared to observe what proportion of $^{32}$P is being accreted by bone, presumably by a non-specific mechanism after breakdown of the conjugate.

In another example, mice bearing xenografted human tumors expressing the antigen recognized by the targeting protein are injected with the labeled protein. After various time intervals mice are sacrificed and dissected, and the ratio of radioactivity found in the tumor and in other tissue is measured.

D. Administration of the $^{32}$P-labeled Targeting Protein

Generally, the dosage of administered $^{32}$P-labeled protein will vary depending upon such factors as the patient's age, weight, height, sex, general medical condition, and previous medical history. Typically, it is desirable to provide the recipient with a dosage of labeled protein which is in the range of from about 1 pg/kg to 10 mg/kg (amount of agent/body weight of patient), although a lower or higher dosage may also be administered.

For therapeutic applications, about 1–50 milligrams of $^{32}$P-labeled protein will be administered, normally daily for a period of several days.

Administration of labeled proteins to a patient can be intravenous, intraarterial, intraperitoneal, intramuscular, subcutaneous, intrapleural, intrathecal, by perfusion through a regional catheter, or by direct intralesional injection. When administering the protein by injection, the administration may be by continuous infusion, or by single or multiple boluses.

The labeled proteins of the present invention can be formulated according to known methods to prepare pharmaceutically useful compositions, whereby immunoconjugates are combined in a mixture with a pharmaceutically acceptable carrier. A composition is said to be a "pharmaceutically acceptable carrier" if its administration can be tolerated by a recipient patient. Sterile phosphate-buffered saline (PBS) is one example of a pharmaceutically acceptable carrier. Other suitable carriers are well-known to those in the art. See, for example, REMINGTON'S PHARMACEUTICAL SCIENCES, 18th Ed. (1990).

For purposes of therapy, a $^{32}$P-labeled protein and a pharmaceutically acceptable carrier are administered to a patient in a therapeutically effective amount. A combination of a $^{32}$P-labeled protein and pharmaceutically acceptable carrier is said to be administered in a "therapeutically effective amount" if the amount administered is physiologically significant. An agent is physiologically significant if its presence results in a detectable change in the physiology of a recipient patient. A targeted therapeutic agent is therapeutically effective if it delivers a higher proportion of the administered dose to the intended target than accretes at the target upon systemic administration of the equivalent untargeted agent.

To be therapeutically effective, the labeled protein and carrier may need to be administered in combination with other therapeutic agents or as part of a broader treatment regimen. Physicians now are currently of the opinion that the effectiveness of targeted therapeutics can often be greatly increased when used in a combination therapy approach. For example, high-dose radioimmunotherapy for B-cell lymphomas, which causes severe hematologic toxicity when used alone, has been shown to be highly effective when used in combination with autologous bone marrow reinfusion. Press et al., "Treatment of Relapsed B Cell Lymphomas with High Dose Radioimmunotherapy and Bone Marrow Transplantation" in CANCER THERAPY WITH RADIOLABELED ANTIBODIES, Goldenberg, Ed. (CRC Press, Boca Raton, 1995) ch. 17. In another example a five-fold enhancement of tumor uptake of a radiolabeled antibody is observed when the tumor is preirradiated. Leichner et al., *Int. J. Radiat. Oncol. Biol. Phys.* 14:1033 (1987). Mechanisms which have been shown to have the potential for improving the clinical efficacy of radioimmunotherapy are also discussed in DeNardo et al., "Overview of Obstacles and Opportunities for Radioimmunotherapy of Cancer" in CANCER THERAPY WITH RADIOLABELED ANTIBODIES, Goldenberg, Ed. (CRC Press, Boca Raton, 1995) ch. 11. Efforts to develop such combination protocols, as well as to investigate dose-limiting side effects and to potentiate and amplify targeting, uptake, and beneficial side effects, are underway in many laboratories and hospitals and are expected to further enhance the utility of targeted therapeutic agents.

Additional pharmaceutical methods may be employed to control the duration of action of the labeled protein in a therapeutic application. Control release preparations can be prepared through the use of polymers to complex or adsorb a protein. For example, biocompatible polymers include matrices of poly(ethylene-co-vinyl acetate) and matrices of a polyanhydride copolymer of a stearic acid dimer and sebacic acid. Sherwood et al., *Bio/Technology*

10:1446–1449 (1992). The rate of release of a $^{32}$P-labeled protein from such a matrix depends upon the molecular weight of the protein, the amount of protein within the matrix, and the size of dispersed particles. Saltzman et al., *Biophysical. J.* 55:163–171 (1989); and Sherwood et al., supra. Other solid dosage forms are described in REMINGTON'S PHARMACEUTICAL SCIENCES, 18th Ed. (1990).

Having now generally described the invention, the same will be more readily understood through reference to the following Examples which are provided by way of illustration, and are not intended to be limiting of the present invention, unless specified.

EXAMPLE 1

Synthesis of 1-(N-Maleimidomethyl)cyclohexane-4-(2-aminoethylacetamide) (MCAA) (6)

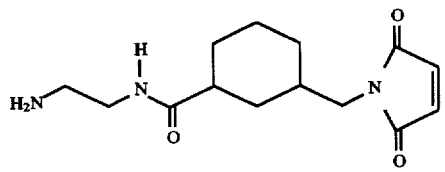

Sulfo-SMCC (1 eq.)(Pierce Chemical Co., Rockford, Ill.) is dissolved in sodium acetate buffer (pH 7) and ethylenediamine dihydrochloride (5 eq.) is added. The reaction is monitored by TLC visualized with fluorescamine. When reaction is complete the reaction mixture is applied directly to a $C_{18}$ reverse-phase HPLC column and eluted with a gradient of acetonitrile in triethanolamine/water, pH 7. The excess ethylene diamine elutes at the solvent front, followed by the desired product. A small amount of double coupled material formed by the condensation of one molecule of ethylenediamine with two molecules of sulfo-SMCC elutes last. The desired material is characterized by $^1$H NMR and IR spectroscopy, mass spectrometry, and elemental analysis.

EXAMPLE 2

Condensation of MCAA with $^{32}$P-labeled adenosine monophosphate (AMP) to form $^{32}$P-AMP-MCAA (7)

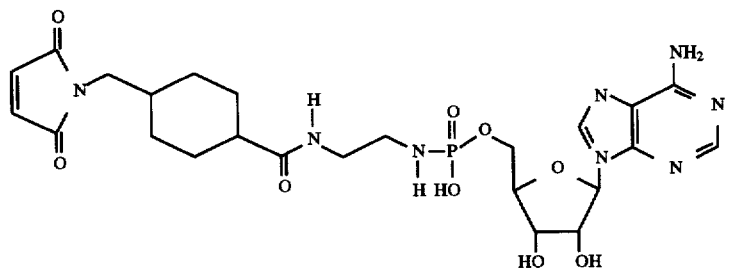

MCAA (1 eq.) and $^{32}$P-AMP (1 eq.) are mixed in aqueous 'butanol, and EDC (1 eq.) is added. The reaction is allowed to proceed at room temperature and is monitored by reverse-phase HPLC on a $C_{18}$ column. When starting materials have disappeared the reaction mixture is purified using a preparative reverse-phase $C_{18}$ column, eluting with a gradient of acetonitrile in sodium phosphate buffer, pH 7.

EXAMPLE 3

Coupling of $^{32}$P-AMP-MCAA to anti-CEA Monoclonal Antibody MN14

MN14 is an IgG which specifically recognizes carcinoembryonic antigen (CEA). MN14 is reduced by addition of 2-mercaptoethanol at pH 8.7 for 10 min at 4° C. to produce two free thiol groups in the hinge region of the antibody. Reduced MN14 is dissolved in sodium phosphate buffer (pH 6) and $^{32}$P-AMP-MCAA (0.5 eq.) is added. Progress of the reaction is monitored by size-exclusion chromatography on a BioSil 250 column (Biorad, Hercules, Calif.) using an in-line radiation detector.

EXAMPLE 4

Measurement of Immunoreactivity of $^{32}$P-labeled MN14

The conjugated antibody, prepared as described in Example 3 above, is applied to a column of CEA (Calbiochem, La Jolla, Calif.) covalently linked to Affigel (Biorad, Hercules, Calif.). The column is eluted with PBS and the radioactivity which elutes from the column is measured and compared to the amount of radioactivity applied to the column. $^{131}$I-labeled MN14, which is known to display the same immunoreactivity as native MN14, is also applied to the column and the same comparison made. Comparison of the bound/non-bound ratios for both labeled antibodies affords a measurement of the effect of the coupling of the $^{32}$P-labeling agent on the immunoreactivity of MN14.

EXAMPLE 5

Measurement of Biodistribution of $^{32}$P-labeled MN14

The conjugated antibody is injected into 35 BALB/c mice at a concentration of 10 mg/kg body weight. Five animals are sacrificed at each time point of 2 h, 4 h, 1,2,3,7, and 14 days. At each time point the mice are dissected to remove all bone tissue, which is solubilized in ethanol/nitric acid. Non-bone tissue is solubilized in TS-1 (Research Products International). Both solubilized samples are added to scintillation fluid and radioactivity measured using a scintillation counter. Bone and non-bone radioactivity is compared at each time point. Increased amounts of radioactivity found in bone indicates increased breakdown of the conjugate.

EXAMPLE 6

Measurement of Tissue Specificity of $^{32}$P-labeled MN14

60 outbred, female, athymic nude mice (Harlan, Indianapolis, Ind.) are injected with LS-174T human tumor cells. After tumors develop in the mice the $^{32}$P-labeled antibody conjugate is injected into one pool of 30 mice and $^{131}$I-labeled MN14 (prepared by the chloramine-T method) is injected into the other 30 mice, both at doses of 10 mg/kg body weight. 5 animals from each pool are sacrificed at each time point of 4 h, 1, 2, 3, 7 and 14 days, and the tumors removed by dissection. The tumor and non-tumor tissue are weighed and solubilized, and the ration of radioactivity found in each fraction determined by β-counting (for $^{32}$P label) and by γ-counting (for $^{131}$I label). Iodine labeling of MN14 is known to have no significant effect on the immunoreactivity of MN14, and therefore the effect of the $^{32}$P labeling on MN14 tumor targeting can be determined by comparing the tumor/non-tumor ratios found with each labeling method.

What is claimed is:

1. A radiolabeled targeting protein comprising a complex of the formula Q—(S)$_m$—L—NR'—P(O)(OH)Y—R wherein P is the $^{32}$P or $^{33}$P isotope, Q is a protein capable of binding specifically to a complementary target molecular species by virtue of a complementarity-determining region thereof, L is a linker moiety, Y is oxygen or a single bond to R, or Y is NR", R, R' and R" are the same or different, and each is an optionally substituted straight-chain or branched-chain alkyl, cycloalkyl, aryl, or heterocyclic group containing from 1 to 20 carbon atoms, or is hydrogen, and m is 1 or 2, or a physiologically acceptable salt thereof.

2. A radiolabeled targeting protein according to claim 1, wherein Q is a monoclonal antibody or antibody fragment.

3. A radiolabeled targeting protein according to claim 2, wherein the thiol group on Q is generated by reduction of a disulfide bond in the hinge region of said monoclonal antibody or antibody fragment.

4. A radiolabeled targeting protein according to claim 1, wherein L is —S—A—, wherein A is an optionally substituted saturated or unsaturated straight-chain or branched-chain alkylene, cycloalkylene, arylene, or divalent heterocyclic group containing from 1 to 20 carbon atoms.

5. A radiolabeled targeting protein according to claim 1, wherein L is —CH$_2$—CO—BD—, wherein B is O, NH, or B is a single bond to C, and wherein D is an optionally substituted saturated or unsaturated straight-chain or branched-chain alkylene, cycloalkylene, arylene, or divalent heterocyclic group containing from 1 to 20 carbon atoms.

6. A radiolabeled targeting protein according to claim 1 where L is

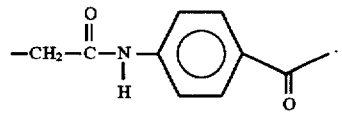

7. A radiolabeled targeting protein according to claim 1 where L is

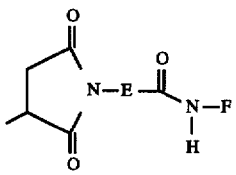

wherein E and F are the same or different, and each is an optionally substituted saturated or unsaturated straight-chain or branched-chain alkylene, cycloalkylene, arylene, or divalent heterocyclic group containing from 1 to 20 carbon atoms.

8. A radiolabeled targeting protein according to claim 7, wherein E is selected from the group consisting of:

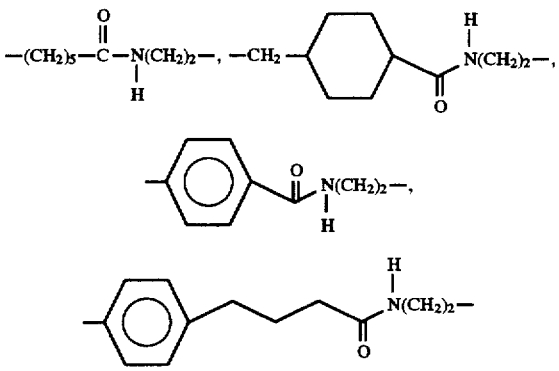

and F is (CH$_2$)$_2$.

9. A radiolabeled targeting protein according to claim 1, wherein YR is selected from the group consisting of 5'—O-adenosine, 5'—O-guanosine, 5'—O-thymidine, 5'—O-cytidine, 5'—O-deoxyadenosine, 5'—O-deoxyguanosine, 5'—O-uridine, 5'—O-deoxycytidine, 5-O-inositol-1,4-bisphosphate and 5-O-inositol-1,3,4-trisphosphate.

10. A pharmaceutical composition, comprising an effective amount of a composition as recited in claim 1, in a pharmaceutically acceptable sterile vehicle.

11. A method of preparing a radiolabeled targeting protein, comprising contacting a protein capable of binding specifically to a complementary target molecular species by virtue of a complementarity-determining region thereof, and containing at least one free thiol group, with a complex of the formula L'—NR'—P(O)(OH)Y—R wherein P is the $^{32}$P or $^{33}$P isotope, L' is a linker moiety comprising a group capable of reacting specifically with said thiol groups on said targeting protein to form a disulfide or thioether linkage, Y is oxygen or a single bond to R, or Y is NR", and R, R', and R" are the same or different, and each is an optionally substituted straight-chain or branched-chain alkyl, cycloalkyl, aryl, or heterocyclic group containing from 1 to 20 carbon atoms, or is hydrogen, or a physiologically acceptable salt thereof.

12. A method for treating a disease in a mammal, comprising administering to a mammal in need thereof a radiolabeled targeting protein comprising a complex of the formula Q—(S)$_m$—L—NR'—P(O)(OH)Y—R wherein P is the $^{32}$P or $^{33}$P isotope, Q is a protein capable of binding specifically to a complementary target molecular species by virtue of a complementarity-determining region thereof, L is a linker moiety, Y is oxygen or a single bond to R, or Y is NR", R, R', and R" are the same or different, and each is an optionally substituted straight-chain or branched-chain alkyl, cycloalkyl, aryl, or heterocyclic group containing from 1 to 20 carbon atoms, or is hydrogen, and wherein m is 1 or 2, or a physiologically acceptable salt thereof.

13. A kit for preparing a radiolabeled targeting protein comprising, in suitable containers, (1) a preparation of a bifunctional cross-linking molecule comprising: a moiety comprising a group capable of reacting specifically with thiol groups on a protein to form a disulfide or thioether linkage, and a primary or secondary amine group; (2) a targeting protein containing at least one thiol group; and (3) at least one reagent for effecting coupling between a phosphate, phosphonate, or phosphoramidate P—OH and said primary amine group.

* * * * *